(12) United States Patent
Wrabetz et al.

(10) Patent No.: US 7,939,288 B2
(45) Date of Patent: May 10, 2011

(54) METHOD FOR DIFFERENTIATING BETWEEN FACTOR XIII DEFICIENCY STATES AND FIBRINOGEN DEFICIENCY STATES BY MEANS OF THROMBELASTOGRAPHIC TECHNIQUES

(75) Inventors: Erhardt Wrabetz, Hochheim (DE); Hubert Metzner, Marburg (DE); Wolfgang Korte, Gallen (CH)

(73) Assignee: CSL Behring GmbH, Marburg (DE)

( * ) Notice: Subject to any disclaimer, the term of this patent is extended or adjusted under 35 U.S.C. 154(b) by 403 days.

(21) Appl. No.: 11/883,916

(22) PCT Filed: Feb. 6, 2006

(86) PCT No.: PCT/EP2006/001015
§ 371 (c)(1),
(2), (4) Date: Aug. 8, 2007

(87) PCT Pub. No.: WO2006/084648
PCT Pub. Date: Aug. 17, 2006

(65) Prior Publication Data
US 2008/0261238 A1    Oct. 23, 2008

(30) Foreign Application Priority Data
Feb. 8, 2005 (DE) .................... 10 2005 005 824

(51) Int. Cl.
*C12Q 1/56* (2006.01)
(52) U.S. Cl. .................. 435/13; 424/145.1; 530/388.25
(58) Field of Classification Search .................... 435/13; 424/145.1; 530/388.25
See application file for complete search history.

(56) References Cited

U.S. PATENT DOCUMENTS

| | | | |
|---|---|---|---|
| 6,245,573 B1 | 6/2001 | Spillert | |
| 2003/0219904 A1 | 11/2003 | Cohen et al. | |
| 2004/0203163 A1* | 10/2004 | Cohen et al. | 436/69 |
| 2004/0214337 A1 | 10/2004 | Kautzky | |
| 2008/0268483 A1* | 10/2008 | Goldenberg et al. | 435/13 |
| 2009/0130645 A1* | 5/2009 | Schubert et al. | 435/2 |

FOREIGN PATENT DOCUMENTS

| | | |
|---|---|---|
| WO | WO 01/07070 A1 | 2/2001 |
| WO | WO 01/96879 A2 | 12/2001 |
| WO | WO 2004/081579 A2 | 9/2004 |
| WO | WO 2004/092742 A1 | 10/2004 |

OTHER PUBLICATIONS

Craft et al., "A Novel Modification of the Thrombelastograph Assay (TEG®) Which Isolates Platelet Function," *The Journal of the American Society of Anesthesiologists, Inc.*, A-148, 2003.

Katori et al., "A Novel Method to Assess Platelet Inhibition by Eptifibatide with Thrombelastograph®," *Anesth. Analg.*, vol. 99, pp. 1794-1799, 2004.
Nielsen et al., "The Impact of Factor XIII on Coagulation Kinetics and Clot Strength Determined by Thrombelastography," *Anesth. Analg.*, vol. 99, pp. 120-123, 2004.
Nielsen et al., "Effects of Coagulation Factor Deficiency on Plasma Coagulation Kinetics Determined via Thrombelastography®: Critical Roles of Fibrinogen and Factors II, VII, X and XII," *ACTA Anaesthesiol. Scand.*, vol. 49, pp. 222-231, 2005.
Calatzis, et al., "A New Technique for Fast and Specific Intraoperative Coagulation Monitoring," XXXIst Congress of the European Society for Surgical Research, Abstract 89, 47-48 (1996).
Finney, et al., "Tridegin, A New Peptidic Inhibitor of Factor XIIIa, from the Blood-Sucking Leech *Haementeria ghilianii*," Biochemical Journal 324:797-805 (1997).
Harding, et al., "Use of Heparinase Modified Thrombelastography in Liver Transplantation," British Journal of Anaesthesia 78:175-179 (1997).
Muto, et al., "Factor XIII Supplement Therapy—Effects on Disturbances of Wound Healing," Biomedical Progress 10(1):16-19 (1997).
Kettner, et al., "Endogenous Heparin-Like Substances Significantly Impair Coagulation in Patients Undergoing Orthotopic Liver Transplantation," Anesthesia & Analgesia 86(4):691-695 (1998).
Pivalizza, et al., "Thromboelastography with Heparinase in Orthotopic Liver Transplantation," Journal of Cardiothoracic and Vascular Anesthesia 12(3):305-308 (1998).
Kettner, et al., "Use of Abciximab-Modified Thrombelastography in Patients Undergoing Cardiac Surgery," Anesthesia & Analgesia 89(3):580-584 (1999).
Shore-Lesserson, et al., "Thromboelastography-Guided Transfusion Algorithm Reduces Transfusions in Complex Cardiac Surgery," Anesthesia & Analgesia 88(2):312-319 (1999).
Mahla, et al., "Thromboelastography for Monitoring Prolonged Hypercoagulability After Major Abdominal Surgery," Anesthesia & Analgesia 92(3):572-577 (2001).
Lauer, et al., "Targeted Inactivation of the Mouse Locus Encoding Coagulation Factor XIII-A: Hemostatic Abnormalities in Mutant Mice and Characterization of the Coagulation Deficit," Thrombosis and Haemostasis 88(6):967-974 (2002).
Prasa, et al., "Hemmstoffe Von Faktor XIIIa," Hämostaseologie, 22(1): 29-33 (2002).
Lang, et al., "Different Effects of Abciximab And Cytochalasin D on Clot Strength in Thrombelastography," Journal of Thrombosis and Haemostasis 2:147-153 (2004). Schroeder, et al., "Influence of Blood Coagulation Factor XIII and FXIII Val34Leu on Plasma Clot Formation Measured by Thrombelastography," Thrombosis Research 104:467-474 (2001).

\* cited by examiner

*Primary Examiner* — Ralph Gitomer
(74) *Attorney, Agent, or Firm* — Finnegan, Henderson, Farabow, Garrett & Dunner, L.L.P.

(57) ABSTRACT

The invention relates to a method for determining a factor XIII deficiency, a method for determining a fibrinogen deficiency, and a method for differentiating between a factor XIII deficiency and a fibrinogen deficiency by means of thrombelastographic techniques. On the basis of the evaluation of the thrombelastographic parameters, a rapid and a selective substitution of factor XIII and/or of fibrinogen in deficiency states is possible.

34 Claims, No Drawings

METHOD FOR DIFFERENTIATING BETWEEN FACTOR XIII DEFICIENCY STATES AND FIBRINOGEN DEFICIENCY STATES BY MEANS OF THROMBELASTOGRAPHIC TECHNIQUES

CROSS REFERENCE TO RELATED APPLICATIONS

This application is a National Phase application of International Application No. PCT/EP2006/001015 filed under the Patent Cooperation Treaty on Feb. 6, 2006, which claims the benefit of German Patent Application No. 102005005824.8, filed Feb. 8, 2005, the disclosures of which are incorporated in their entireties.

INTRODUCTION

The invention relates to a method for determining a factor XIII deficiency, a method for determining a fibrinogen deficiency, and also a method for differentiating between a factor XIII deficiency and a fibrinogen deficiency by means of thromb-elastographic techniques. Based on the evaluation of thrombelastographic parameters, a rapid and selective substitution of factor XIII and/or of fibrinogen in deficiency states is possible.

BACKGROUND OF THE INVENTION

Thrombelastography (TEG) is a diagnostic method which mechanically investigates clot formation or dissolution in an oscillating system. Here, either a vessel (cup) is in oscillating motion around a measuring rod (pin) (conventional TEG) or else the vessel is fixed and the pin is brought into oscillating rotational motion (ROTEG or ROTEM). The mechanical forces arising between the cup and pin are recorded. As soon as the blood or plasma starts to clot, a variation in the initial measurement signal occurs. Both designs will be designated here as TEG.

TEG is employed for the investigation of blood or plasma in order to determine clotting-relevant parameters (TEG parameters), such as the period of time up to reaching a first significant clot formation with an amplitude of 2 mm (clotting or reaction time r), the period of time up to reaching a clot thickness of an amplitude of 20 mm (k value), the rate at which the clot is formed (alpha angle), the mechanical properties of the clot at maximum amplitude (MA) or at any other desired point in time, the period of time up to MA (TMA), or the period of time until the clot strength has fallen again to a certain value because of fibrinolysis. Clinically, TEG is employed as a diagnostic measure, inter alia, for the assessment of coagulopathy, for example in heart surgery, in liver transplantation, major abdominal surgery and as a quasi-bedside test in perioperative clotting management (Kettner S C et al. (1999) Anesth Analg; 89: 580-584; Shore-Lesserson L et al. (1999), Anesth Analg; 88: 312-319; Harding S A et al. (1997), Br J Anaesth: 175-179; Kettner S C et al. (1998), Anesth Analg; 86: 691-695, Pivalizza E G et al. (1998), J Cardiothorac Vasc Anesth; 12: 305-308, Mahla E et al. (2001), Anesth Analg; 92: 572-577; Calatzis A N et al. (1996), Eur Surg Res; 28: S1 (89).

TEG is available in addition to the standard clotting diagnostics (inter alia Quick, aPTT, platelet count, AT III, fibrinogen, D dimers, bleeding time), which are more time-consuming for the determination of the values for rapid information about bleeding trends. This is particularly of importance if coagulopathies occur in the course of extensive surgical interventions or after polytraumata, since serious haemostasis disorders can rapidly lead to the development of secondary tissue damage and are often resistant to a conventional haemostatic therapy based on a more time-consuming standard clotting diagnosis.

The TEG parameters are influenced by a number of factors which are designated below as thrombelastographically relevant factors. Thrombelastographically relevant factors are especially fibrinogen, factor XIII, and blood platelet levels and components of the fibrinolytic system such as plasmin, plasmin activators, and plasmin inhibitors. For instance, fibrinogen, as a clotting substrate, correlates with the clot stability. This can be clearly shown in the thrombelastogram. Moreover, factor XIII likewise modulates, by means of the crosslinkage of the fibrin formed from the fibrinogen, the mechanical properties of the clot and restricts its lysis (P. Lauer et al. (2002), Thromb Haemost; 88: 97-974). The two effects have not been clearly separable from one another in thrombelastography until now, since they equally influence central measurement of a thrombelastogram. Both fibrinogen and factor XIII significantly influence the parameters clotting time (r), maximum clot strength, alpha angle as a measure of the rate of clot formation and the lysis time of the clot (Nielsen V G et al. (2004), Anesth Analg; 99: 120-123). Since in acquired deficiency states such as in polytraumata or relatively major surgical interventions the fibrinogen and the factor XIII levels do not necessarily decrease equally, up to now a selective therapeutic intervention clearly in favour of one or the other component on the basis of the thrombelastogram is not possible. It would therefore be desirable if a method was available which would allow, on the basis of rapid TEG diagnosis, a determination whether a bleeding tendency is based on a factor XIII deficiency and/or on a fibrinogen deficiency.

BRIEF SUMMARY OF THE INVENTION

The present investigations were based on the objective of making possible, by means of thrombelastographic techniques, a determination of the content of thrombelastographically relevant factors such as, for example, factor XIII and fibrinogen, preferably by making possible a clear differentiation of the influencing variables factor XIII and fibrinogen in haemostasis disorders and assessing their respective contribution to the haemostasis disorder in order to allow thereby a selective therapeutic intervention by substitution of the missing factor.

The objective was achieved by developing a procedure which allows the determination of the deficiency of one or more thrombelastographically relevant factors, by comparing certain TEG parameters in the presence and absence of inhibitors of the corresponding thrombelastographically relevant factors, and/or by comparing certain TEG parameters in the presence and absence of activators of the corresponding thrombelastographic factors, and/or by comparing certain TEG parameters with and without addition of the corresponding thrombelastographically relevant factors.

In particular, the content of the thrombelastographic factors factor XIII and fibrinogen can be differentiated by carrying out the measurement with and without inhibitors for factor XIII and/or with and without addition of factor XIII and/or by addition of activators of fibrinogen. By comparing the TEG parameters of these approaches the influence of the individual factors can be determined and the degree of necessary substitution of the individual components for achieving stable haemostasis can be determined. By this means, for example, intraoperative massive haemorrhages can be treated even more selectively and rapidly and risks of postoperative haemostasis disorders, and under certain circumstances wound healing disorders caused thereby, can be recognized and likewise specifically avoided by substitution of the individual components. Further components which influence the TEG parameters, such as platelet count and activity or fibrinolytic activity, can be suppressed by known procedures.

DETAILED DESCRIPTION OF THE INVENTION AND VARIOUS EMBODIMENTS

By comparing the TEG parameters, such as, for example, the reaction time (r), the maximum amplitude (MA), the time until the achievement of the maximum amplitude (TMA) or the alpha angle in the presence or absence of factor XIII inhibitors, a differentiation can be made between a factor XIII deficiency and other deficiency states as a cause of haemostasis disorders.

For the inhibition of factor XIII, for example, antibodies against factor XIII, peptide inhibitors such as tridegin (Finney S. et al. (1997), Biochem J. 324: 797-805) or low molecular weight inhibitors of factor XIII, such as, for example, putrescin, dansylcadaverine or others (Prasa D. et al. (2002), Hamostaseologie 22: 29-33) are used. The factor XIII inhibitor or the concentration of the factor XIII inhibitor is preferably to be chosen such that the factor XIII activity in the sample investigated is specifically and completely inhibited.

The lower the factor XIII level in a patient, the lower the difference here between the values of a TEG parameter which is measured in the presence and absence of a factor XIII inhibitor. The evaluation of the difference in the TEG parameters in the presence and absence of a factor XIII inhibitor allows a conclusion whether a relatively slight, moderate, or severe factor XIII deficiency is present. By supplementing a whole blood sample obtained from a patient having factor XIII deficiency with different amounts of factor XIII and by comparing the thrombelastogram in the presence and absence of an inhibitor of factor XIII in these samples, the effect can also be shown in the form of a standard curve. A curve obtained in this way allows the factor XIII level in a patient sample to be determined from the difference of a TEG parameter in the presence and absence of a factor XIII inhibitor. Preferably, corresponding standard curves are plotted at different fibrinogen contents.

By relating the difference in the patient sample in the presence and absence of a factor XIII inhibitor to the ratio of the TEG parameter (with addition of inhibitor) of the patient plasma to a control sample, it becomes possible to put into perspective the measurement difference and thus take into consideration different fibrinogen levels, e.g. by formation of the following term in case of the maximum amplitude:

$(MA_{sample\ without\ inh.} - MA_{sample\ with\ inh.})$
$(MA_{control\ with\ inh.}/sample\ with\ inh.)$.

Analogous standard curves can also be obtained with platelet-poor and platelet-rich plasma. A value below 70% of the standard value of factor XIII in plasma is considered a factor XIII deficiency state, which should be treated (T. Muto et al. (1997), Biomed. Progress 10: 16-19).

Alternatively, a factor XIII deficiency can also be detected by a reverse procedure, by comparing a sample with and without addition of factor XIII by TEG. Unlike the use of factor XIII inhibitors, a small difference in the TEG parameters here indicates a standard value of the factor XIII in the sample, whereas large differences point to a severe factor XIII deficiency. As described above, on the basis of factor XIII-deficient whole blood or plasma also for this procedure standard curves can be plotted which allow more accurate diagnosis. In the case of addition of factor XIII, at the minimum an amount is added which would adjust to 100% factor XIII even in a complete factor XIII deficiency. Preferably, even higher still F XIII amounts are employed, compared to which the F XIII contained in the sample is negligible.

In order to improve differential diagnostics with respect to fibrinogen levels, which also strongly influence the TEG parameters, a further aspect of the present invention is the determination of the fibrinogen level in the blood of the patient with the aid of thrombelastographic parameters.

One method of evaluating a possible fibrinogen deficiency consists of treating a whole blood sample, or a platelet-poor or platelet-rich plasma, with proteases which activate fibrinogen, but are not reactive towards factor XIII. For instance, by using batroxobin, a protease isolated from snake venom, the fibrinogen of the sample can be converted to fibrin (without crosslinkage by factor XIII) and in comparison to a standard control (blood or plasma of healthy donors) a fibrinogen decrease can be detected. It can be advantageous here to work in the presence of hirudin in order to avoid factor XIII activation in the course of the measurement. When carrying out a TEG investigation of this type, the amount of protease which is added should be sufficient in order to activate the fibrinogen within a few minutes and to polymerize it with formation of a clot. In the case of batroxobin, the fibrinogen should be converted to the AA fibrinogen within a few minutes, which polymerizes to give a clot. The greater the difference to the normal value of the TEG parameter investigated, the greater the fibrinogen deficiency in the patient sample. The activation of fibrinogen advantageously takes place in the presence of factors inhibiting the activation of factor XIII, as, for example, in the presence of thrombin inhibitors such as, for example, hirudin.

Since platelets can also influence the clot properties and thus the TEG parameters in whole blood, the performance of the differential diagnostics with simultaneous exclusion of platelet effects is a further preferred aspect of this invention. For example, the use of platelet-poor plasma is possible, since the differentiation of fibrinogen and factor XIII is possible in principle both in whole blood and in plasma. In the case of plasma, a surface reagent, such as, for example, either aPTT reagent or tissue factor reagent, should then be used for the initiation of the clotting. Alternatively, when using platelet-rich plasma or whole blood, the determination of the TEG parameters can be carried out in the presence of platelet antagonists, such as, for example, cytochalasin and/or abciximab, to exclude platelet effects. A particularly preferred embodiment is the elimination of the platelet effects by a combination of cytochalasin D and abciximab (Lang et al.; J Thromb Haemost. 2004; 2(1): 147-53).

Since the thrombolytic system can also influence the clot properties and thus the TEG parameters, the inhibition of the components of the thrombolytic system is advantageous to exclude influences of the thrombolytic system. A further aspect of this invention is therefore to carry out the described differential diagnostics with simultaneous inhibition of thrombolytic activities such as, for example, plasmin or plasma activators, or with simultaneous activation of plasmin inhibitors. A preferred embodiment here is to carry out the TEG in the presence of aprotinin, α2-antiplasmin, or similar inhibitors, or alternatively low molecular weight inhibitors.

A particularly preferred embodiment is to carry out the TEG with simultaneous exclusion of the platelet influence and also the inhibition of the thrombolytic system.

The procedures described allow the effects of the platelets and of the thrombolytic system to be eliminated in the thrombelastographic system and a differentiation to be carried out between a factor XIII deficiency and a fibrinogen deficiency. The particular advantage here lies in the fact that the factor XIII and fibrinogen levels can be determined promptly and near to the patient by means of TEG and the diagnostic result thus can be directly converted therapeutically.

The use of factor XIII inhibitors also makes it possible, by means of TEG in the presence and absence of platelet antagonists or fibrinolysis inhibitors, to switch off factor XIII as an influencing factor on these measurements and thus to diagnose platelet effects more clearly.

The invention relates, in addition to the method for the determination of factor XIII levels and fibrinogen levels, to the differentiation of fibrinogen deficiency and factor XIII deficiency states, also to a diagnostic kit comprising factor XIII inhibitors and/or factor XIII and/or fibrinogen activators and optionally further agents such as platelet antagonists (e.g. cytochalasin D, abciximab) and inhibitors of the fibrinolytic system. By means of multichannel measurements, it is possible to obtain a sophisticated statement about the substitution requirement of factor XIII and/or fibrinogen.

In one embodiment of a diagnostic kit, the reagents are already initially introduced into the TEG cups here.

EXAMPLES

1. Inhibition of Factor XIII in Plasma by Addition of Factor XIII Antibodies

In order to quantitatively determine the influence of factor XIII, in one experiment standard human plasma with or without addition of factor XIII inhibitors (anti-factor XIII IgG preparation) was analysed by means of TEG. The clotting reaction was accelerated by addition of an aPTT reagent. The test batch contained: NaCl soln or anti-factor XIII IgG preparation in different dilutions (30 µl), Pathromtin SL (50 µl, Dade Behring), standard human plasma (200 µl) and 200 mM CaCl$_2$ soln (20 µl). The reagents were pipetted into the cup at 37° C. and the TEG measurement was started using Haemoscope apparatuses. The following measurement parameters were analysed: R, alpha angle, maximum amplitude and time until the achievement of the maximum amplitude.

TABLE 1

Inhibition of factor XIII in plasma by addition of factor XIII antibodies

|  |  | R (sec) | Angle (°) | MA (mm) | TMA (sec) | Mean values from |
|---|---|---|---|---|---|---|
| Control (without F XIII Ab) |  | 133.8 | 70.7 | 16.7 | 721.3 | n = 8 |
| Anti FXIII A IgG prep. | 1:3 | 217.5 | 53.3 | 7.1 | 272.5 | n = 2 |
|  | 1:10 | 157.5 | 61.7 | 9.9 | 382.5 | n = 2 |
|  | 1:30 | 152.5 | 67.5 | 15.1 | 605.0 | n = 2 |
|  | 1:100 | 120.0 | 69.2 | 16.3 | 687.5 | n = 2 |

The results show that the factor XIII inhibition clearly has an effect on the TEG parameters measured. Accordingly, a comparative approach (+/−factor XIII inhibitor) in a patient sample with a reduced maximum amplitude would allow an estimation of whether an adequate amount of factor XIII is still present in the sample or whether this is significantly reduced (with reduced factor XIII levels the effect of the factor XIII inhibitor addition would be lower than with normal factor XIII levels).

2. Investigation of Plasma and Whole Blood by Parallel Measurements in the Presence and Absence of Low Molecular Weight Factor XIII Inhibitors For the quantitative determination of the influence of factor XIII, standard human plasma with or without addition of low molecular weight factor XIII inhibitors was analysed by means of TEG. The clotting reaction was started or accelerated by addition of a tissue factor reagent. The test batch contained: 200 µl of plasma, 30 µl of NaCl soln (control) or inhibitor solution in different dilutions, 50 µl of tissue factor reagent. (Thromborel S, Dade Behring) and 20 µl of calcium chloride solution (200 mmol/l). The reagents were pipetted into the cup at 37° C. and the TEG measurement was started with Haemoscope apparatuses. Alternatively, the calcium chloride can also be already added to the tissue factor reagent and the reaction thus started. The measurement parameters of reaction time (R), alpha angle, maximum amplitude (MA) and time to achieve the maximum amplitude (MA) were determined and evaluated.

As F XIII inhibitors for the differentiation of the F XIII content, putrescin, histidine, dansylcadaverine or 1,3,4,5-tetramethyl-2-[(2-oxopropyl)thio]imidazolium chloride in different dilutions were employed. The investigations carried out here with plasma are in principle also applicable to whole blood.

TABLE 2

Effect of putrescine, monodansylcadaverine and histamine on TEG parameters when using standard human plasma.

| Concentration in the test (µg/ml) | R: sec | Angle: ° | MA: mm | TMA: sec |
|---|---|---|---|---|
| Putrescine |  |  |  |  |
| 1.07 | 22.5 | 73.1 | 17.2 | 452.5 |
| 3.21 | 17.5 | 73.7 | 15.9 | 277.5 |
| 10.7 | 20.0 | 73.4 | 18.7 | 672.5 |
| 32.1 | 25 | 73.0 | 16.9 | 585.0 |
| 107 | 15 | 73.0 | 16.5 | 505.0 |
| 321 | 20 | 72.8 | 15.8 | 400.0 |
| 1.071 | 25 | 69.5 | 13.6 | 405.0 |
| 3.214 | 32.5 | 72.6 | 13.9 | 327.5 |
| Monodansylcadaverine |  |  |  |  |
| 0.32 | 20.0 | 74.0 | 18.1 | 655.0 |
| 1.07 | 22.5 | 74.9 | 18.4 | 610.0 |
| 3.21 | 20.0 | 74.7 | 19.1 | 657.5 |
| 10.7 | 25.0 | 74.4 | 18.4 | 560.0 |
| 32.1 | 17.5 | 74.4 | 17.3 | 562.5 |
| 107 | 32.5 | 76.9 | 18.7 | 237.5 |
| 321 | 20.0 | 71.0 | 15.1 | 490.0 |
| 536 | 27.5 | 70.3 | 13.3 | 370.0 |
| Histamine |  |  |  |  |
| 1.07 | 20.0 | 73.4 | 17.8 | 592.5 |
| 3.21 | 22.5 | 75.0 | 17.9 | 527.5 |
| 10.7 | 20.0 | 74.8 | 19.2 | 622.5 |
| 32.1 | 22.0 | 73.9 | 17.2 | 472.5 |
| 107 | 17.5 | 73.5 | 16.9 | 462.5 |
| 321 | 20.0 | 72.7 | 15.5 | 430.0 |
| 1.071 | 15.0 | 70.3 | 14.0 | 492.5 |
| 3.214 | 25.0 | 71.9 | 13.0 | 182.5 |
| Control |  |  |  |  |
| (physiol. NaCl solution) | 25.6 | 75.6 | 19.7 | 572 |

TABLE 3

Effect of 1,3,4,5-tetramethyl-2-[(2-oxo-propyl)thio]imidazolium chloride on the TEG parameters).

| Concentration in the test (µg/ml) | R: sec | Angle: ° | MA: mm | TMA: sec |
|---|---|---|---|---|
| 1,3,4,5-Tetramethyl-2-[(2-oxopropyl)thio]-imidazolium chloride | | | | |
| 0.033 | 22.5 | 79.6 | 21.5 | 177.5 |
| 0.10 | 22.5 | 79.0 | 18.5 | 140.0 |
| 0.33 | 22.5 | 77.0 | 14.9 | 77.5 |
| 1.00 | 22.5 | 75.4 | 13.1 | 77.5 |
| 3.33 | 22.5 | 74.0 | 12.4 | 77.5 |
| Control | | | | |
| (physiol. NaCl solution) | 27.5 | 77.7 | 21.6 | 520.0 |

The inhibitors investigated can inhibit the action of F XIII and the relevant TEG parameters such as, for example, maximum amplitude (MA), respond significantly to the still available F XIII content. In this manner, F XIII-deficient plasma can be identified, since plasma of this type does not show the effects of the F XIII inhibitors or only shows it to a limited extent. The above investigations reveal as preferred inhibitor concentrations those in which the parameters influenced by F XIII, such as the maximum amplitude MA, no longer clearly decrease or increase. For 1,3,4,5-tetramethyl-2-[(2-oxopropyl)thio]imidazol-ium chloride, this is, for example, a final concentration of 1 µg/ml, particularly preferably of about 3 µg/ml or higher.

3. Differential Investigation for the Diagnosis of a Deficiency of Fibrinogen and Factor XIII Hypothetical Example Differential TEG analysis for the estimation of the clotting-relevant residual capacity of factor XIII and fibrinogen or further factors. The total range of conditions can be investigated or a choice made according to the respective problem.

Experimental batch:
a) unchanged sample,
b) sample in the presence of factor XIII anti-bodies,
c) sample clotted by batroxobin (e.g. in the presence of hirudin)
d) sample in the presence of platelet antagonists (in the case of whole blood or platelet-rich plasma)
e) sample in the presence of aprotinin
f) sample in the presence of aprotinin and platelet antagonists (in the case of whole blood or platelet-rich plasma)
g) samples in the presence of F XIII inhibitor, platelet antagonists and fibrinolysis inhibitor (in the case of whole blood or platelet-rich plasma)

A comparison is carried out against historical TEG measurements with normal blood or normal plasma in the presence or absence of the corresponding additions.

The invention claimed is:

1. A method for determining whether a subject's bleeding disorder is based on a factor XIII and/or fibrinogen deficiency with a sample of blood or plasma of unknown factor XIII and fibrinogen levels from the subject, comprising:
   (a) providing at least two samples of blood or plasma, wherein at least one sample is from the subject; and
      (i) preparing a factor XIII inhibitor sample by adding factor XIII inhibitor to the sample from the subject and preparing a factor XIII inhibitor control sample by providing another sample from the subject without adding factor XIII inhibitor; and/or
      (ii) preparing a factor XIII sample by adding factor XIII to the sample from the subject and preparing a factor XIII control sample by providing another sample from the subject without adding factor XIII; and/or
      (iii) preparing a fibrinogen sample by adding fibrinogen activator to the sample from the subject and preparing a fibrinogen control sample by adding fibrinogen activator to control blood or plasma not from the subject;
   (b) performing thrombelastography (TEG) on all the samples to measure at least one TEG parameter in the samples, wherein the at least one TEG parameter is the same in all the samples; and
   (c) correlating the at least one TEG parameter in the samples to one another to determine whether the subject has a factor XIII and/or fibrinogen deficiency, wherein:
      (i) if there is no substantial difference between the values of the at least one TEG parameter in the factor XIII inhibitor sample and the factor XIII inhibitor control sample, the subject has a factor XIII deficiency;
      (ii) if there is a substantial difference between the values of the at least one TEG parameter in the factor XIII sample and the factor XIII control sample, the subject has a factor XIII deficiency;
      (iii) if there is a substantial difference between the values of the at least one TEG parameter in the fibrinogen sample and the fibrinogen control sample, the subject has a fibrinogen deficiency.

2. The method according to claim 1 for determining whether a subject has a factor XIII deficiency comprising: preparing a factor XIII inhibitor sample by adding factor XIII inhibitor to the sample from the subject and preparing a factor XIII inhibitor control sample by providing another sample from the subject without adding factor XIII inhibitor; performing TEG on the samples; and correlating the at least one TEG parameter in the samples, wherein if there is no substantial difference between the values of the at least one TEG parameter in the factor XIII inhibitor sample and the factor XIII inhibitor control sample, the subject has a factor XIII deficiency.

3. The method according to claim 2, wherein the factor XIII inhibitor is poly- or monoclonal antibodies.

4. The method according to claim 2, wherein the factor XIII inhibitor is a peptide inhibitor.

5. The method according to claim 2, wherein the factor XIII inhibitor is a low molecular weight inhibitor.

6. The method according to claim 1 for determining whether a subject has a factor XIII deficiency, comprising: preparing a factor XIII sample by adding factor XIII to the sample from the subject and preparing a factor XIII control sample by providing another sample from the subject without adding factor XIII; performing TEG on the samples; and correlating the at least one TEG parameter in the samples, wherein if there is a substantial difference between the values of the at least one TEG parameter in the factor XIII sample and the factor XIII control sample, the subject has a factor XIII deficiency.

7. The method according to claim 1 for determining whether a subject has a fibrinogen deficiency, comprising: preparing a fibrinogen sample by adding fibrinogen activator to the sample from the subject and preparing a fibrinogen control sample by adding fibrinogen activator to control blood or plasma; performing TEG on the samples; and correlating the at least one TEG parameter in the samples, wherein if there is a substantial difference between the values of the at least one TEG parameter in the fibrinogen sample and the fibrinogen control sample, the subject has a fibrinogen deficiency.

8. The method according to claim 1, wherein the fibrinogen activator is protease, which is not reactive towards factor XIII.

9. The method according to claim 1, wherein the fibrinogen activator is batroxobin.

10. A method for differentiating between factor XIII deficiency and fibrinogen deficiency in a subject, comprising:
   (a) determining whether the subject has a fibrinogen deficiency by:
      (i) preparing a fibrinogen sample by providing a sample of blood or plasma from the subject, and adding fibrinogen activator;
      (ii) preparing a fibrinogen control sample by adding fibrinogen activator to control blood or plasma not from the subject;
      (iii) performing thrombelastography (TEG) on all the samples to measure at least one TEG parameter in the samples, wherein the at least one TEG parameter is the same in all the samples; and
      (iv) correlating the at least one TEG parameter in the samples to one another to determine whether the subject has a fibrinogen deficiency, wherein if there is a substantial difference between the values of the at least one TEG parameter in the fibrinogen sample and the fibrinogen control sample, the subject has a fibrinogen deficiency;
   (b) determining whether the subject has a factor XIII deficiency by:
      (i) providing two samples of blood or plasma from the subject; and
         (1) preparing a factor XIII inhibitor sample by adding factor XIII inhibitor to a sample from the subject and preparing a factor XIII inhibitor control sample by providing another sample from the subject without adding factor XIII inhibitor; or
         (2) preparing a factor XIII sample by adding factor XIII to a sample from the subject and preparing a factor XIII control sample by providing another sample from the subject without adding factor XIII;
      (ii) performing TEG on all the samples to measure at least one TEG parameter in the samples, wherein the at least one TEG parameter is the same in all the samples; and
      (iii) correlating the at least one TEG parameter in the samples to one another to determine whether the subject has a factor XIII deficiency, wherein
         (1) if there is no substantial difference between the values of the at least one TEG parameter in the factor XIII inhibitor sample and the factor XIII inhibitor control sample, the subject has a factor XIII deficiency; or
         (2) if there is a substantial difference between the values of the at least one TEG parameter in the factor XIII sample and the factor XIII control sample, the subject has a factor XIII deficiency; and
   (c) comparing any factor XIII deficiency and fibrinogen deficiency, thereby differentiating between factor XIII deficiency and fibrinogen deficiency in the subject.

11. The method according to claim 10, wherein in determining whether a subject has a factor XIII deficiency, the method comprises preparing a factor XIII inhibitor sample by adding factor XIII inhibitor to a sample from the subject and preparing a factor XIII inhibitor control sample by providing another sample from the subject without adding factor XIII inhibitor.

12. The method according to claim 11, wherein the factor XIII inhibitor is poly- or monoclonal antibodies.

13. The method according to claim 11, wherein the factor XIII inhibitor is a peptide inhibitor.

14. The method according to claim 11, wherein the factor XIII inhibitor is a low molecular weight inhibitor.

15. The method according to claim 11, wherein the fibrinogen activator is protease, which is not reactive towards factor XIII.

16. The method according to claim 11, wherein the fibrinogen activator is batroxobin.

17. The method according to claim 11, wherein, in determining whether a subject has a fibrinogen deficiency, the samples have added hirudin.

18. The method according to claim 10, wherein in determining whether a subject has a factor XIII deficiency, the method comprises preparing a factor XIII sample by adding factor XIII to a sample from the subject and preparing a factor XIII control sample by providing another sample from the subject without adding factor XIII.

19. The method according to claim 18, wherein the fibrinogen activator is protease, which is not reactive towards factor XIII.

20. The method according to claim 18, wherein the fibrinogen activator is batroxobin.

21. The method according to claim 18, wherein, in determining whether a subject has a fibrinogen deficiency, the samples have added hirudin.

22. The method according to claim 10, wherein all the samples are platelet-poor plasma.

23. The method according to claim 22, wherein all the samples have added inhibitor of the thrombolytic system.

24. The method according to claim 23, wherein the inhibitor of the thrombolytic system is aprotinin.

25. The method according to claim 10, wherein all the samples are whole blood or platelet-rich plasma with added platelet antagonists.

26. The method according to claim 25, wherein all the samples have added inhibitor of the thrombolytic system.

27. The method according to claim 26, wherein the inhibitor of the thrombolytic system is aprotinin.

28. The method according to claim 10, wherein all the samples have added inhibitor of the thrombolytic system.

29. The method according to claim 28, wherein the inhibitor of the thrombolytic system is aprotinin.

30. The method of claim 10, wherein the TEG parameter is one or more of:
   (a) r, period of time up to reaching a first clot formation with an amplitude of 2 mm,
   (b) k, period of time up to reaching a clot thickness of an amplitude of 20 mm,
   (c) α angle, rate at which a clot is formed,
   (d) MA, mechanical properties of a clot at maximum amplitude,
   (e) TMA, period of time up to MA, and
   (f) period of time until clot strength has fallen because of fibrinolysis.

31. The method according to claim 10, wherein, in determining whether a subject has a fibrinogen deficiency, the at least one TEG parameter in the fibrinogen control sample is a historical TEG measurement of blood or plasma of normal fibrinogen levels.

32. The method according to claim 10, wherein the samples have added inhibitor of the thrombolytic system.

33. The method according to claim 32, wherein the inhibitor of the thrombolytic system is aprotinin.

34. A method for differentiating between factor XIII deficiency and fibrinogen deficiency in a subject comprising:
(a) determining whether the subject has a fibrinogen deficiency by:
(i) preparing a fibrinogen sample by providing a sample of blood or plasma from the subject, and adding aprotinin and batroxobin;
(ii) preparing a fibrinogen control sample by adding aprotinin and batroxobin to control blood or plasma not from the subject;
(iii) performing thrombelastography (TEG) on all the samples to measure at least one TEG parameter in the samples, wherein the at least one TEG parameter is the same in all the samples; and
(iv) correlating the at least one TEG parameter in the samples to one another to determine whether the subject has a fibrinogen deficiency, wherein if there is a substantial difference between the values of the at least one TEG parameter in the fibrinogen sample and the fibrinogen control sample, the subject has a fibrinogen deficiency;
(b) determining whether the subject has a factor XIII deficiency by:
(i) providing two samples of blood or plasma from the subject; and
(1) preparing a factor XIII inhibitor sample by adding aprotinin and poly- or monoclonal antibodies to a sample and preparing a factor XIII inhibitor control sample by adding aprotinin without adding poly- or monoclonal antibodies to another sample; or
(2) preparing a factor XIII sample by adding aprotinin and factor XIII to a sample and preparing a factor XIII control sample by adding aprotinin without adding factor XIII to another sample;
(iii) performing TEG on all the samples to measure at least one TEG parameter in the samples, wherein the at least one TEG parameter is the same in all the samples; and
(iii) correlating the at least one TEG parameter in the samples to one another to determine whether the subject has a factor XIII deficiency, wherein
(1) if there is no substantial difference between the values of the at least one TEG parameter in the factor XIII inhibitor sample and the factor XIII inhibitor control sample, the subject has a factor XIII deficiency; or
(2) if there is a substantial difference between the values of the at least one TEG parameter in the factor XIII sample and the factor XIII control sample, the subject has a factor XIII deficiency; and
(c) comparing any factor XIII deficiency and fibrinogen deficiency thereby differentiating between factor XIII deficiency and fibrinogen deficiency in the subject.

* * * * *

UNITED STATES PATENT AND TRADEMARK OFFICE
CERTIFICATE OF CORRECTION

| | | |
|---|---|---|
| PATENT NO. | : 7,939,288 B2 | Page 1 of 1 |
| APPLICATION NO. | : 11/883916 | |
| DATED | : May 10, 2011 | |
| INVENTOR(S) | : Erhardt Wrabetz | |

It is certified that error appears in the above-identified patent and that said Letters Patent is hereby corrected as shown below:

On the Title Page, Item (75), in the Inventors, line 3,
"Gallen (CH)" should read --St. Gallen (CH)--.

Signed and Sealed this
Sixth Day of September, 2011

David J. Kappos
*Director of the United States Patent and Trademark Office*